(12) United States Patent
Rayan et al.

(10) Patent No.: US 8,586,625 B2
(45) Date of Patent: Nov. 19, 2013

(54) DERIVATIVES OF TAXOL AND CLOSELY RELATED COMPOUNDS

(76) Inventors: Anwar Rayan, Kabul (IL); Taher Nassar, Turan (IL)

( * ) Notice: Subject to any disclaimer, the term of this patent is extended or adjusted under 35 U.S.C. 154(b) by 463 days.

(21) Appl. No.: 12/863,271

(22) PCT Filed: Jan. 16, 2009

(86) PCT No.: PCT/IB2009/050158
§ 371 (c)(1),
(2), (4) Date: Jul. 16, 2010

(87) PCT Pub. No.: WO2009/090614
PCT Pub. Date: Jul. 23, 2009

(65) Prior Publication Data
US 2010/0298421 A1  Nov. 25, 2010

Related U.S. Application Data

(60) Provisional application No. 61/021,344, filed on Jan. 16, 2008.

(51) Int. Cl.
| | | |
|---|---|---|
| *A01N 43/26* | (2006.01) | |
| *A61K 31/385* | (2006.01) | |
| *C07D 339/02* | (2006.01) | |
| *C07D 341/00* | (2006.01) | |
| *C07D 409/00* | (2006.01) | |
| *A01N 37/10* | (2006.01) | |
| *A61K 31/235* | (2006.01) | |

(52) U.S. Cl.
USPC .............................. 514/440; 549/39; 514/533

(58) Field of Classification Search
None
See application file for complete search history.

(56) References Cited

U.S. PATENT DOCUMENTS

| | | |
|---|---|---|
| 6,340,701 B1 | 1/2002 | Chari et al. |
| 6,448,278 B2 | 9/2002 | Bailey et al. |
| 2002/0198161 A1 | 12/2002 | Brash et al. |
| 2011/0144163 A1* | 6/2011 | Kingston et al. .............. 514/337 |

OTHER PUBLICATIONS

International Search Report issued in PCT/IB2009/050158.
International Preliminary Report on Patentability issued in PCT/IB2009/050158.

* cited by examiner

*Primary Examiner* — James D Anderson
*Assistant Examiner* — William Lee
(74) *Attorney, Agent, or Firm* — Browdy and Neimark, PLLC

(57) ABSTRACT

A cytotoxic composition in which two moieties are conjugated covalently. A first moiety is a tax moiety, selected from the group consisting of taxanes, taxane derivatives, and or other closely relative compounds. A second moiety is an acid moiety selected from the group consisting of lipoic acid, acetylcysteine, compounds having an acidic group.

10 Claims, 6 Drawing Sheets

Fig. 1: LC-MS analysis of paclitaxel-lipoate shows the m/e=1042
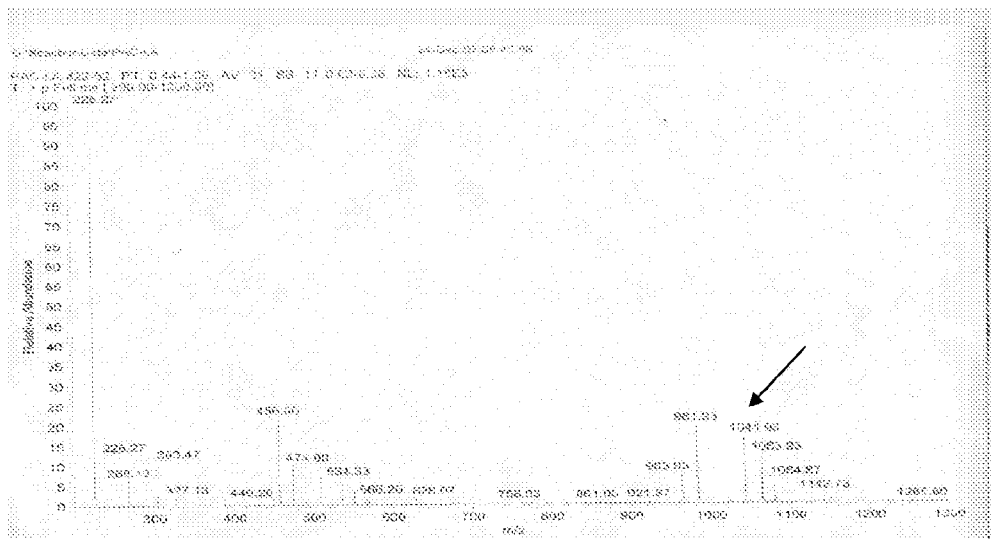
Fig. 2: H-NMR of paclitaxel-lipoate. Acylation of hydroxyl at position 2' is characterized by disappearance of the hydroxyl proton resonance at 3.6 ppm and a shift of the resonance of the proton alpha to the hydroxyl group from 4.8 ppm to 5.6 ppm.
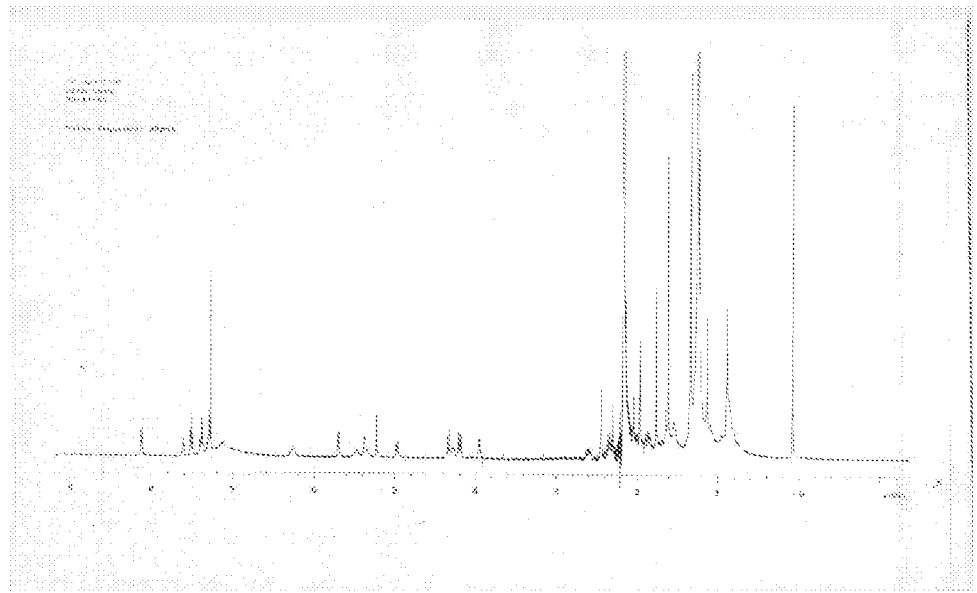

Fig. 3a: Calculated $EC_{50}$ of paclitaxel and CX001 (PACLP) on HeLa are 9 and 1.5 µg/ml respectively.
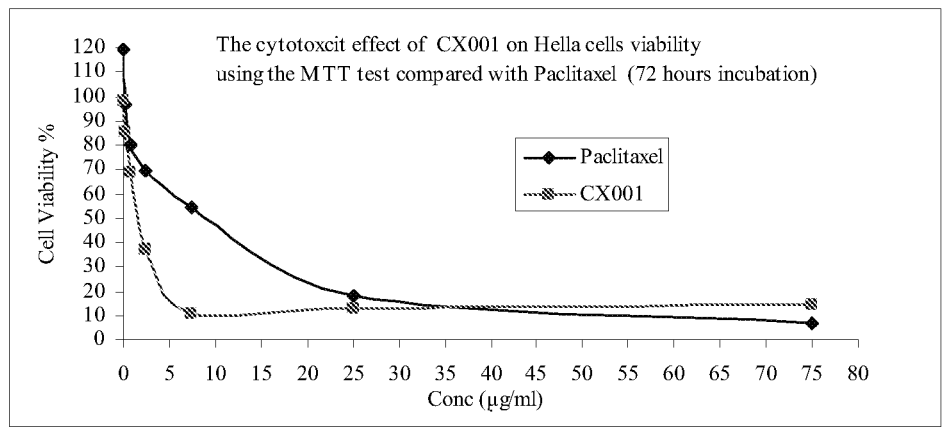
Fig. 3b: Calculated $EC_{50}$ of paclitaxel and CX001 (PACLP) on Caco-2 carcinoma of the colon are 9 and 1.5 µg/ml respectively.
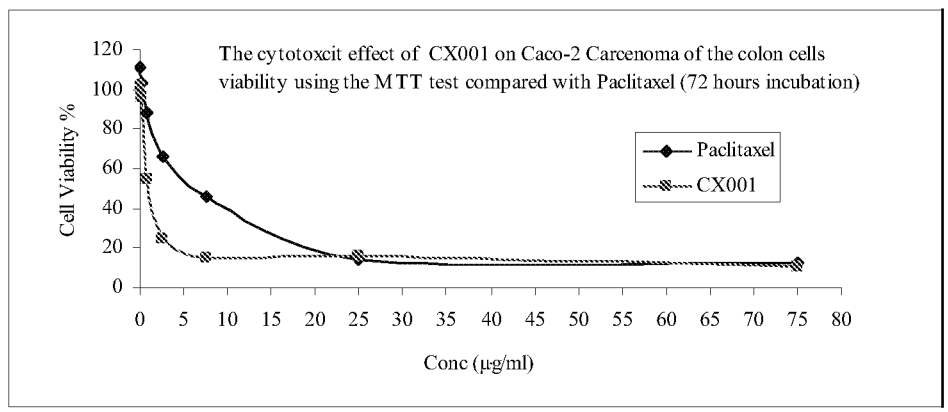

Fig. 3c: Calculated $EC_{50}$ of paclitaxel and CX001 (PACLP) on prostate carcinoma are 12 and 3.5 µg/ml respectively.
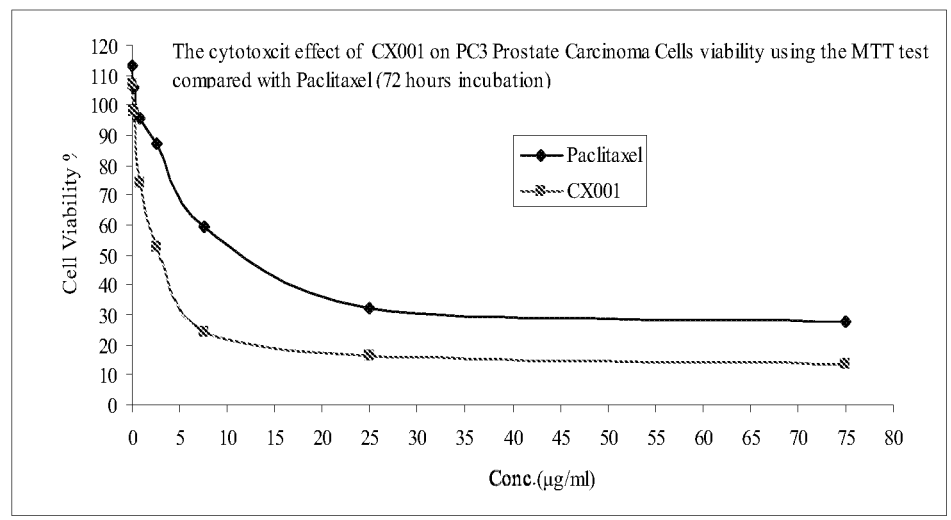
Fig. 3d: Calculated $EC_{50}$ of paclitaxel and CX001 (PACLP) on CAPAN are 11 and 5 µg/ml respectively.
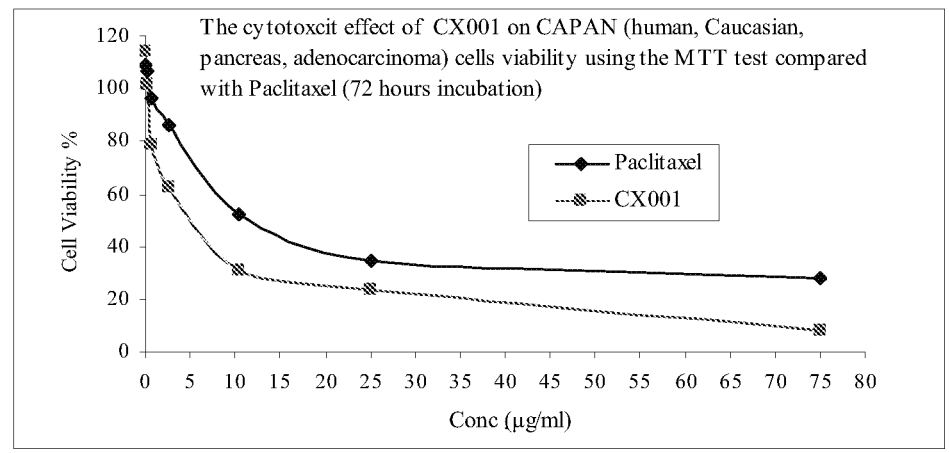

Fig. 3e: Calculated $EC_{50}$ of paclitaxel and CX001 (PACLP) on lung cancer are 5.5 and 2.5 μg/ml respectively.
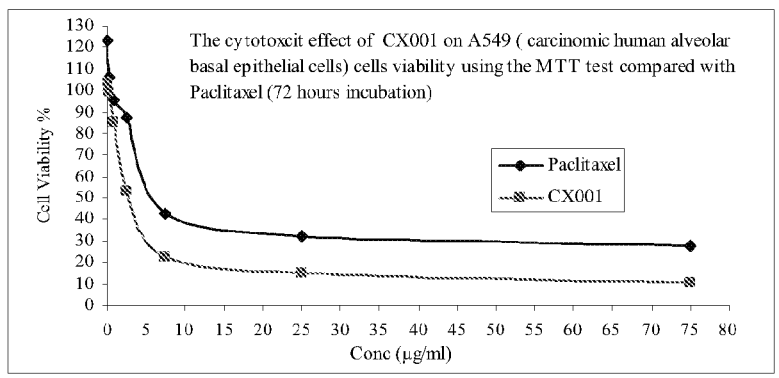
Fig. 3f: Calculated $EC_{50}$ of paclitaxel and CX001 (PACLP) on breast carcinoma are 19 and 2 μg/ml respectively.
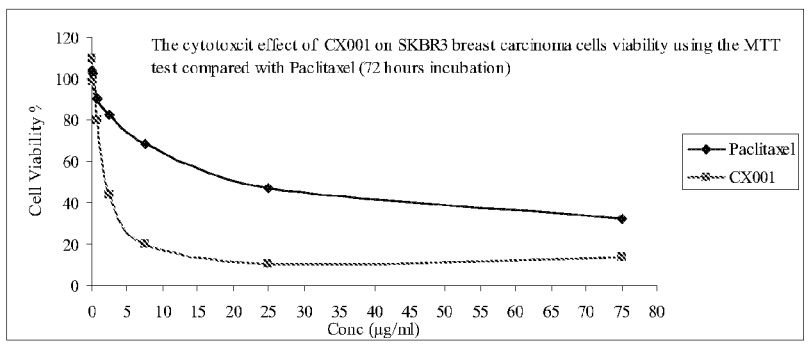

Fig. 4: Toxicity on endothelial cells
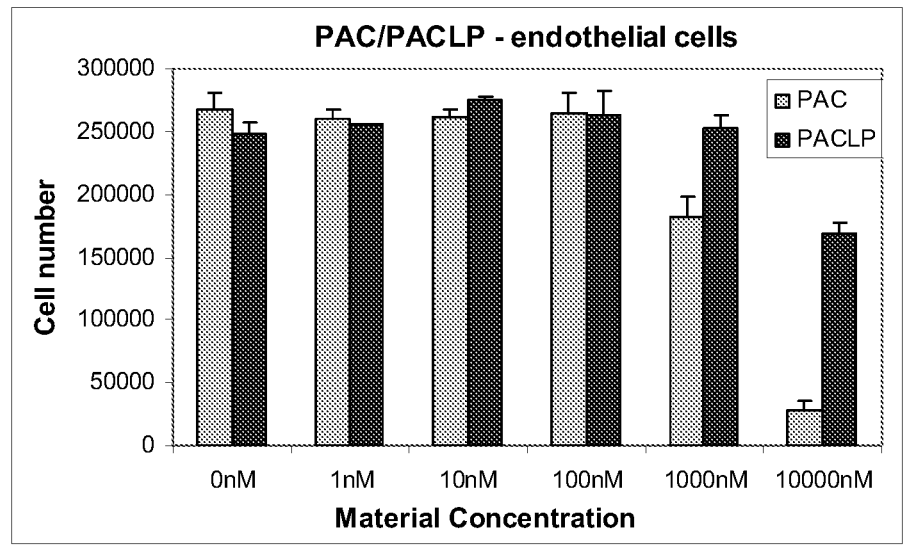
Fig. 5: toxicity on hepatocyte cell line HepG2
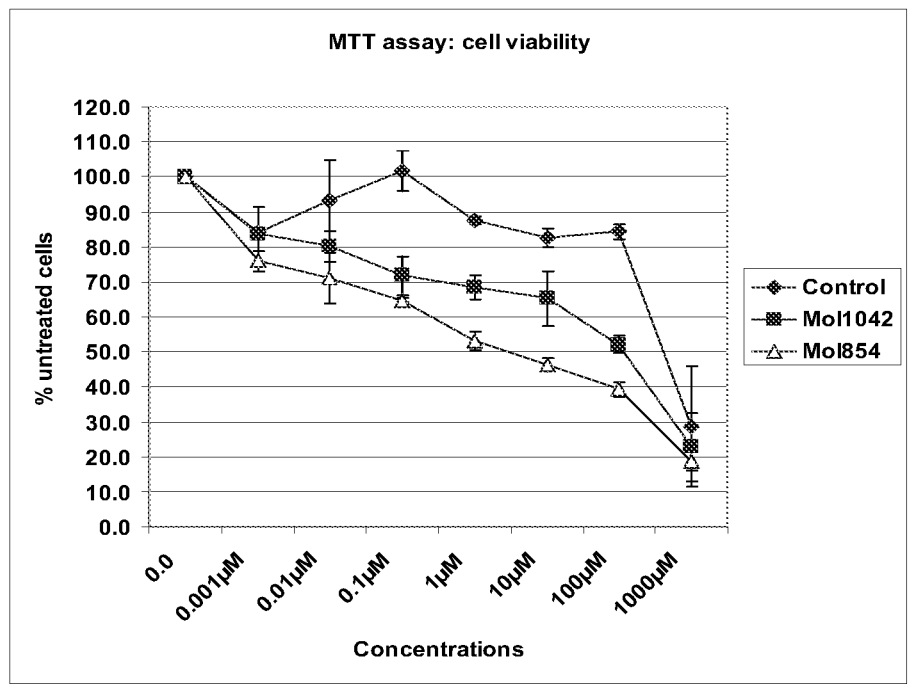

Fig. 6: number of survived animals after 4 weeks. MDL1100 index for PACLP while MDL850 index for paclitaxel.
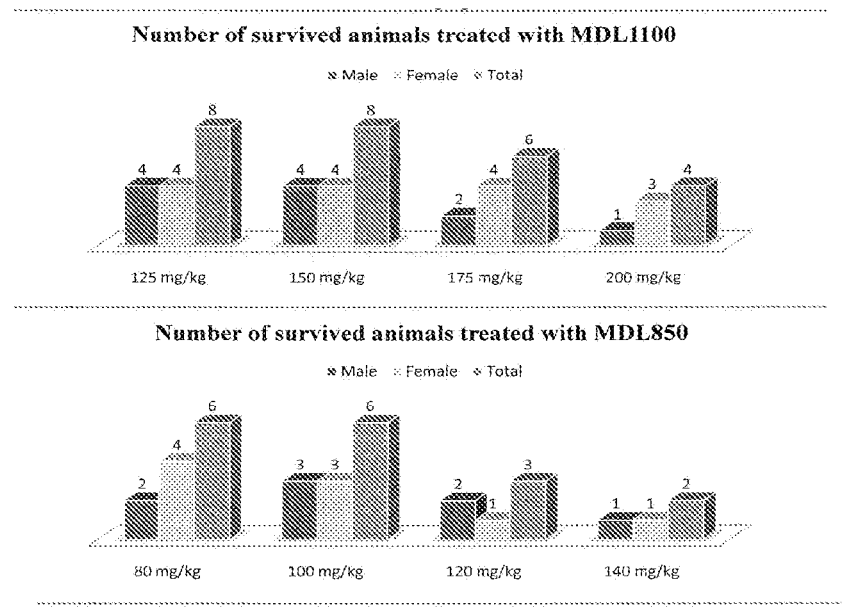

DERIVATIVES OF TAXOL AND CLOSELY RELATED COMPOUNDS

The present application claims priority from U.S. provisional patent application Ser. No. 61/021,344, filed Jan. 16, 2008, entitled "NOVEL DERIVATIVES OF TAXOL AND CLOSELY RELATED COMPOUNDS AND THERAPEUTICS USES THEREOF". The aforementioned application is incorporated herein by this reference.

FIELD OF THE INVENTION

The present invention relates to a compound used for therapeutic treatment and more particularly to a use of paclitaxel derivatives or closely related compounds as anti-tumor agents.

BACKGROUND OF THE INVENTION

Taxanes such as paclitaxel and docetaxel are considered as important anticancer drugs. They are mitotic inhibitors used in cancer chemotherapy, which act by interfering in the normal microtubule growth during cell division. They bind to β-tubulin subunits of microtubules, preventing depolymerization of the mitotic spindle, thereby leading to cell cycle arrest, inhibits cell replication and eventually promoting apoptosis. Paclitaxel has displayed significant antitumor activity against non-small-cell lung cancer (NSCLC), ovarian, head and neck tumors and breast cancer as well as in preventing restenosis. Despite the excellent antitumor properties of these drugs, paclitaxel, as well as the other closely related compounds suffer from significant disadvantages among which is low water solubility, certain toxic effects (myelosuppression, neutropenia, hypersensitivity reactions and fluid retention). Such side effects limit the clinically administrable dose.

Matrix metalloproteinases (MMPs) are enzymes that regulate cell-matrix composition. They are involved in normal and pathological process, including cancer, inflammation, arthritis, cardiovascular diseases and others. Cancer growth and dissemination involve multiple Matrix metalloproteinases that direct the interactions of tumor cells with the surrounding matrix. Indeed, inhibition of metalloproteinases reduces the malignant potential of experimental tumors. MMP-2 (Matrix metallopeptidase 2 (gelatinase A, 72 kDa gelatinase, 72 kDa type IV collagenase)) has attracted attention since it was found as a key component of cancer cell migration across collagen by a mechanism involving CBD-mediated MMP-2 interactions with collagen. Thus, it is associated with is tumor invasion and formation of metastases. Metastasis is defined as spread of cancer through the bloodstream and lymphatic system to other parts of the body where they form metastases. Lipoic acid is a chiral compound consisting of a carboxylic acid and a cyclic disulfide. It is an essential factor for aerobic life and a common dietary supplement. It is an antioxidant needed for the activity of enzyme complexes such as those of pyruvate dehydrogenase and glycine decarboxylase. In its reduced form (Dihydrolipoic acid) it influences a number of cell processes by direct radical scavenging, recycling of other antioxidants, increasing glutathione synthesis and modulating transcription factor activity.

SUMMARY OF THE INVENTION

The present invention provides a conjugate composition of matter of taxenes and acid groups, such as lipoic acid and/or MMPs inhibitors. The conjugates, in general, are able to combine with other antitumor agents to treat a mammalian cell proliferating disease, such as cancer and reduce side-effects. Furthermore, the conjugates may have anti-metastasis and/or antiangiogenic activities.

The conjugates may reduce side-effects of other antitumor agents as well. They are effective in somatic and autonomic neuropathies in diabetes, normalizes the endoneural blood-flow, reduce oxidative stress and improve vascular dysfunction. In another aspect of the present invention, a method for treating cancers is provided. The method includes administering a therapeutically effective amount of the conjugates to a patient in need of such treatment.

The present invention provides pharmaceutical composition of taxenes and acid groups, such as lipoic acid and/or MMPs inhibitors.

BRIEF DESCRIPTION OF THE DRAWING

FIG. 1 is a LC-MS analysis of paclitaxel-lipoate shows the m/e=1042

FIG. 2 is a H-NMR of paclitaxel-lipoate. Acylation of hydroxyl at position 2' is characterized by disappearance of the hydroxyl proton resonance at 3.6 ppm and a shift of the resonance of the proton alpha to the hydroxyl group from 4.8 ppm to 5.6 ppm.

FIG. 3a is a response curve showing effect of PACLP/paclitaxel in in-vitro tests in 6 cancer cell lines, calculated $EC_{50}$ of Paclitaxel and CX001 (PACLP) on HeLa cell line are 9 and 1.5 μg/ml respectively.

FIG. 3b is a response curve showing effect of PACLP/paclitaxel in in-vitro tests in 6 cancer cell lines, calculated $EC_{50}$ of paclitaxel and CX001 (PACLP) on Caco-2 carcinoma of the colon are 9 and 1.5 μg/ml respectively.

FIG. 3c is a response curve showing effect of PACLP/paclitaxel in in-vitro tests in 6 cancer cell lines, calculated $EC_{50}$ of paclitaxel and CX001 (PACLP) on prostate carcinoma are 12 and 3.5 μg/ml respectively.

FIG. 3d is a response curve showing effect of PACLP/paclitaxel in in-vitro tests in 6 cancer cell lines, calculated $EC_{50}$ of paclitaxel and CX001 (PACLP) on CAPAN are 11 and 5 μg/ml respectively.

FIG. 3e is a response curve showing effect of PACLP/Paclitaxel in in-vitro tests in 6 cancer cell lines, Calculated $EC_{50}$ of paclitaxel and CX001 (PACLP) on lung cancer are 5.5 and 2.5 μg/ml respectively.

FIG. 3f is a response curve showing effect of PACLP/paclitaxel in in-vitro tests in 6 cancer cell lines, calculated $EC_{50}$ of paclitaxel and CX001 (PACLP) on breast carcinoma are 19 and 2 μg/ml respectively.

FIG. 4 is a response curve showing toxic effect on endothelial cells.

FIG. 5 is a response curve showing toxic effect on hepatocyte cell line HepG2.

FIG. 6 is a response curve showing the number of survived animals after 4 weeks. MDL1100 index for PACLP while MDL850 index for paclitaxel.

DETAILED DESCRIPTION OF THE PRESENT INVENTION

In the present invention, compounds for treatment of mammalian cell proliferating disease, e.g., cancer, reduced side-effects and prevent metastasis are provided.

Procedure:

The product in accordance with the present invention is a conjoint of at least two different bioactive compounds, such as taxanes or other closely related chemical molecules, with a second bioactive organic moiety "X" which is any compound or composition of matter which can inhibit MMPs, such as MMP-2 inhibitors. Typically, tax is one of the following taxanes: paclitaxel, docetaxel, cephalomannine, 10-Deacetyl cephalomannine, 10-Deacetyl taxol, 7-Epi-10-deacetyl taxol, 7-Epi-10-deacetyl cephalomannine, 10-Deacetyl baccatn III and other derivatives of taxol. paclitaxel, has three hydroxyl groups to which the second organic moiety can be attached. These hydroxyl groups are located at the C-2', C-7 and C-1 positions, with their relative order of reactivity generally believed to be C-2'>C-7>>C-1 (from most reactive to least reactive). As a result, an esterified conjugate is created, via hydroxyl group C-2' position and/or C-7 position and/or C-1 position respectively.

Exemplary conjugates are as follows: C-2'-X paclitaxel (moiety X attached to paclitaxel at the C-2' position), 7-X paclitaxel (moiety X attached to paclitaxel at the C-7 position), 1-X paclitaxel (moiety X attached to paclitaxel at the C-1 position), (C-2'-X, C-7-X, C-1-X) paclitaxel.

In one embodiment of the present invention, the moiety "X", potential MMP-2 inhibitor, correspond to a general formula as depicted herein bellow:

In which Z is zinc chelating group

Y represents an acidic group such as but not limited to $SO_2$, $PO_2$, $CO$, $NO_2$ R represents any chemical group that link between the zinc chelating group Z and the acidic group Y which is attached to tax.

In some embodiments, moiety "X" is:

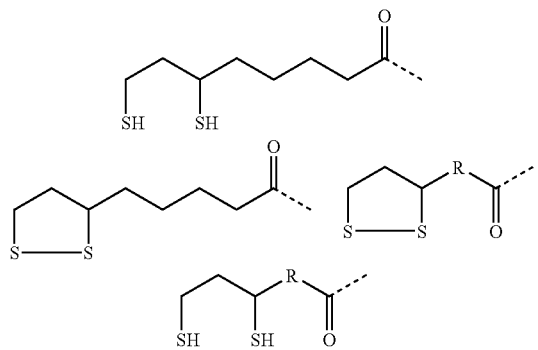

In which R is C1 to C6

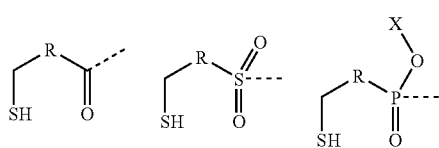

In which R is C1 to C6
X represents H, Hydrocarbon, or

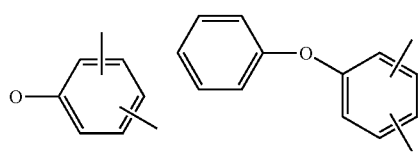

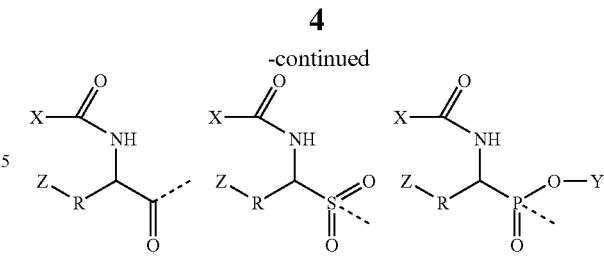

In which Z is a zinc chelating group such as but not limited:
—SH, —CO2, —PO3, CONHOH, —SO$_3$, —SOR
R represents a C1 to C6 radical.
X represents a hydrophobic chemical moiety such as but not limited to methyl, ethyl.
Y represents an H, or other Hydrocarbon moiety such as:

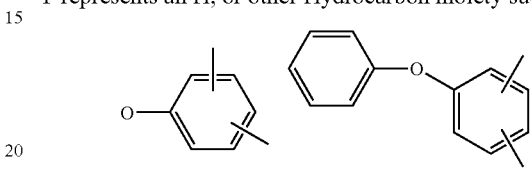

EXAMPLE 1

A Conjugate Product

In one embodiment of the present invention, the conjugate of the tax is an acid compound, The tax is a taxol derivative compound represented by tax or any pharmaceutically acceptable salt thereof.
Wherein:
The acid compound—represents MMP-2 inhibitor such as lipoic acid or another compound with an acidic group. The acid compound also has zinc binding properties and together with tax can bind to zinc matrix, such as zinc matrix metalloproteinases. For example, acid compound and tax bind to MMP-2 through the reduced form of lipoic acid.
An exemplary conjugate product is depicted herein bellow:
Paclitaxel-lipoate (PACLP) is a product of conjugation of lipoate with taxol derivatives at C-2'-OH position. The effect of PACLP has been tested experimentally on 6 cancer cell lines, and shown a greater anti-tumor activity is compared to the free paclitaxel. The compound PACLP correspond to the following formula:

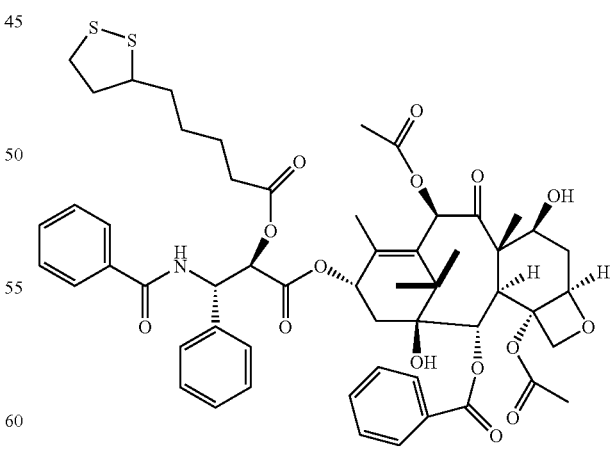

Synthesis of Paclitaxel-Lipoate

Paclitaxel-lipoate was synthesized from paclitaxel (Farmachem, Lugano, Switzerland) and lipoic acid (Sigma, St.

Louis, Mo., USA) in a single step that coupled lipoate to paclitaxel at the 2'-hydroxyl position. To a solution of paclitaxel (35 mg; 41 μmmol) in dry methylene chloride (2.5 ml) under nitrogen were added 4-dimethylaminopyridine (5 mg; 41 μmmol), 1, 3-dicyclohexylcarbodiimide (16.9 mg; 82 μmmol), and lipoic acid (8.5 mg; 41 μmol). The reaction mixture was stirred at ambient temperature for 2 h. After dilution with diethyl ether, the reaction mixture was washed with 5% aqueous hydrochloric acid, water, and saturated aqueous sodium chloride. The mixture was dried (sodium sulfate) and concentrated. Radial chromatography (silica gel; ethyl acetate-hexane 1:1) of the residue gave 45 mg (90%) of solid paclitaxel-lipoate. The product was analysed using LC-MS as shown in FIG. 3 and H-NMR as shown in FIG. 4.

Results of Biological Experiments

Cancer cells, HeLa, Caco-2, PC3 prostate, CAPAN, A549, SKBR3 were maintained in a humidified atmosphere at 37° C. and gassed with 5% $CO_2$ in air in air. The cells were incubated with various concentrations of paclitaxel and PACLP. The in vitro cytotoxicity of the drugs was measured by a proliferation assay utilizing tetrazolium dye, MTT ([3-(4,5-dimethyldiazol-2-yl)-2,5 diphenyl tetrazolium bromid). The experiments were carried out with cells in the exponential growth phase.

Results of these experiments are presented in graphs 3a-3f, indicating the IC50, (the concentration found to inhibit about fifty percent of the growth of the cancer cell lines).

Effect of Paclitaxel and PACLP on Endothelial Cell Proliferation

The test was conducted using endothelial cells of human (H-1044 EC p7 naïve). 70,000 cells were grown in each well. After the cells have adhered for 3 hours, the material (paclitaxel or PACLP) was added to the cells. After 48 hours of cell growth the cells were detached by trypsin and counted. The results are set in.

Toxicity on Hepatocyte Cell Line HepG2

PACLP and paclitaxel were evaluated in vitro using hepatocyte cell line HepG2. Cells were cultured in 96 well plates at a cell density of 20000 cell/well and treated with increasing concentrations of both PACLP and paclitaxel (0-1000 μM) for 72 h. Control cells were treated with an absolute ethanol, diluted in the same way as the tested substances. Cytotoxicity was measured using the MTT test. All experiments were carried out in triplicates and each test was repeated three times.

$CD_{50}$ (the cytotoxic concentration leading to reduction of 50% of the cell number compared to untreated cells) was at concentration of 5 μM and 100 μM, and 500 μM for paclitaxel, PACLP, and the solvent, respectively.

Some observations become apparent from the results of the toxicity test. Firstly, paclitaxel-lipoate (PACLP) was somewhat more effective than paclitaxel in cancer cell lines. Secondly, PACLP was less cytotoxic for endothelial cells of human (HSVEC 29 p8 naïve) and hepatocyte cell line HepG2. The results are set in FIG. 5.

In Vivo Tests

LD50 for PACLP and Paclitaxel Using Balb/c Mice

Balb/c mice were divided into 9 groups, 8 mice in each group (4 males and 4 females). Group one, the control group, were given 50 μl solvent with 150 μL normal saline. Groups 2, 3, 4 and 5 were given 125, 150, 175, 200 mg/kg of PACLP respectively. Groups 6, 7, 8 and 9 were given 80, 100, 120, 140 mg/kg of paclitaxel respectively. Mice were observed 4 weeks after injection. The results are set in FIG. 6. Most of the animals died within the first week after treatment. Paclitaxel treated mice show swelling and redness before death.

Although embodiments of the invention has been set forth in detail, one skilled in the art will appreciate that numerous changes and modifications may be made without departing from the spirit and scope of the present invention.

The invention claimed is:

1. A compound which is an ester of paclitaxel and lipoic acid wherein the esterification is at the C-2' hydroxyl, C-7 hydroxyl or C-1 hydroxyl of paclitaxel.

2. A pharmaceutical composition comprising a compound according to claim 1.

3. The pharmaceutical composition of claim 2, further comprising an anti-mammalian cell proliferating disease agent.

4. The pharmaceutical composition of claim 3, wherein said mammalian cell proliferating disease is cancer.

5. A method for treating cancer comprising administering to a patient in need of such treatment a therapeutically effective amount of a compound according to claim 1.

6. The compound of claim 1, wherein the carbon atom at position 1 of the lipoic acid is linked via an oxygen atom to the carbon atom at position 2' of the paclitaxel.

7. The pharmaceutical composition of claim 2, wherein the carbon atom at position 1 of the lipoic acid is linked via an oxygen atom to the carbon atom at position 2' of the paclitaxel.

8. The pharmaceutical composition of claim 2, further comprising an anti-mammalian cell proliferating disease agent.

9. The pharmaceutical composition of claim 8, wherein said mammalian cell proliferating disease is cancer.

10. The method of claim 5, wherein the carbon atom at position 1 of the lipoic acid is linked via an oxygen atom to the carbon atom at position 2' of the paclitaxel.

* * * * *